US00PP18050P2

(12) United States Plant Patent
Hanes

(10) Patent No.: US PP18,050 P2
(45) Date of Patent: Sep. 18, 2007

(54) ***PELARGONIUM* PLANT NAMED 'FREE ORCH'**

(50) Latin Name: ***Pelargonium peltatum* L'Héritier**
Varietal Denomination: Free Orch

(75) Inventor: Mitchell E. Hanes, Morgan Hill, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 11/370,392

(22) Filed: Mar. 7, 2006

(51) Int. Cl.
*A01H 5/00* (2006.01)

(52) U.S. Cl. ..... Plt./332
(58) Field of Classification Search ..... Plt./332
See application file for complete search history.

*Primary Examiner*—Anne Marie Grunberg
*Assistant Examiner*—Georgia Helmer
(74) *Attorney, Agent, or Firm*—Jondle & Associates, P.C.

(57) ABSTRACT

A new *pelargonium* plant particularly distinguished by deep, lavender-purple, double flowers, small to medium-sized, semi-spherically shaped inflorescences, medium-green foliage with weak zonation, a compact, round and well-branched plant habit with an early flowering response, is disclosed.

1 Drawing Sheet

Genus and species: *Pelargonium peltatum* L'Héritier.
Variety denomination: 'Free Orch'.

BACKGROUND OF THE NEW PLANT

The present invention comprises a new and distinct cultivar of *pelargonium,* botanically known as a *Pelargonium peltatum* L'Héritier, and hereinafter referred to by the cultivar name 'Free Orch'. The new cultivar was propagated from a seedling resulting from the cross of the female parent '8736-3', a cherry-rose-flowered proprietary *pelargonium* plant (unpatented) and the male parent '8732-5' (unpatented) a proprietary *pelargonium* plant having lavender flowers.

The new cultivar was created in 2002 in Gilroy, Calif. and has been asexually reproduced repeatedly by vegetative cuttings and tissue culture in Gilroy, Calif. and Hillscheid, Germany over a three-year period. The present invention has been found to retain its distinctive characteristics through successive asexual propagations.

Plant Breeder's Rights for this cultivar were applied for in Canada on Mar. 29, 2005 and with the European Union on Sep. 20, 2005.

SUMMARY OF THE INVENTION

The following are the most outstanding and distinguishing characteristics of this new cultivar when grown under normal horticultural practices in Gilroy, Calif. and Hillscheid, Germany.

1. Deep lavender-purple, double flowers;
2. Small to medium-sized, semi-spherically-shaped inflorescences;
3. Medium-green foliage with weak zonation;
4. Compact plant habit;
5. A rounded and well-branched plant habit; and
6. An early flowering response.

DESCRIPTION OF THE PHOTOGRAPH

This new *pelargonium* plant is illustrated by the accompanying photograph which shows overall plant habit including inflorescences, buds, and foliage of the plant; the colors shown are as true as can be reasonably obtained by conventional photographic procedures. The photograph is of an above view of three 22-week-old plants grown in a greenhouse in mid-Summer in Hillscheid, Germany.

DESCRIPTION OF THE NEW CULTIVAR

The following detailed description sets forth the distinctive characteristics of 'Free Orch'. The data which define these characteristics were collected from asexual reproductions carried out in Hillscheid, Germany. The plant history was taken on 13-week old plants which were planted as rooted cuttings in 12-cm pots in late May 2005 and grown in a greenhouse. The plants were pinched once. Color readings were taken under natural light in mid-May from flowers grown in the greenhouse. Color references are primarily to The R.H.S. Colour Chart of The Royal Horticultural Society of London (R.H.S.) (2001).

DETAILED BOTANICAL DESCRIPTION

Classification:
- *Family.*—Geraniaceae.
- *Botanical.*—*Pelargonium peltatum* L'Héritier.
- *Common name.*—Ivy geranium.

Parentage:
- *Female parent.*—'8736-3' a proprietary cherry-rose-flowered *pelargonium* plant (unpatented).
- *Male parent.*—'8732-5', a proprietary *pelargonium* plant having lavender flowers (unpatented).

Growth:
- *Form.*—Shrub, self-branching, low spreading to decumbent and trailing habit, compact and small.
- *Branching habit.*—8.6 branches per plant.
- *Height* (*measured from the top of the soil, excluding the inflorescence*).—13.2 cm.
- *Width* (*horizontal plant spread*).—23.2 cm.

*Plant size in late summer (plant radius, measured from the plant base to the tips).*—30 week-old plant developed branches of 35 cm in length.

*Time to produce a finished flowering plant.*—About 11 to 12 weeks for a 12-cm to 14-cm pot in the Spring.

*Outdoor plant performance.*—Plants continuously flower; a count in early September of 30-week old plants in Hillscheid, Germany produced about 9 to 10 inflorescences per plant.

*Time to initiate and develop roots.*—About 24 days at 20° C.

*Root description.*—Fibrous.

Leaves:

*Arrangement.*—Opposite on flowering branches.

*Immature leaf color.*—Upper surface: RHS 143A (grass-green). Lower surface: Between RHS 143C and RHS 144A.

*Mature leaf color.*—Upper surface: Intermediate between RHS 137D to RHS 143A (grass-green). Lower surface: Between RHS 143C and RHS 144A.

*Size.*—Length: 4.4 cm. Width: 7.7 cm.

*Apex.*—Rounded.

*Base.*—Cordate.

*Shape.*—Ivy-shaped, with moderate, rounded lobes, with the lowest lobes possibly overlapping.

*Margin.*—Usually entire.

*Texture.*—Upper surface: Smooth and glabrous, slightly glossy. Lower surface: Protruding veins in palmate arrangement, pubescent.

*Zonation color.*—RHS 147A (brownish-green), weak distinctness.

*Zonation diameter.*—Close around the leaf base. Inner diameter: 0.7 cm. Outer diameter: 2.0 cm.

*Venation type.*—Palmate.

*Venation color.*—RHS 145A (pale-green).

*Petioles.*—Color: RHS 143C (light-green). Length: 3 cm to 4 cm. Diameter: 0.2 cm. Texture: Covered with sparse, short hairs.

Stems:

*Stem color.*—RHS 143B (green), occasionally anthocyanin in parts is RHS 184B.

*Length.*—17.5 cm.

*Diameter (at mid-point).*—About 0.4 cm.

*Internode length.*—Mostly 1.0 cm to 1.5 cm, occasionally up to 3.5 cm.

*Texture.*—Appears smooth, glabrous.

Inflorescence bud:

*Shape.*—Nearly round to elliptical.

*Size.*—Length: 1.4 cm. Width: 1.1 cm.

*Color of sepals (just before petals unfold).*—RHS 143C (light-green).

*Color of petals (just before petals unfold).*—RHS N71D (purple).

Inflorescence:

*Blooming habit.*—Plants continuously flower.

*Inflorescence type.*—An umbel composed of 7 to 9 flowers.

*Umbel.*—Shape: Semi-spherical, relatively tight. Diameter: 8.5 cm. Height (depth): 5.0 cm.

*Lastingness of umbel on the plant.*—About 14 to 16 days.

*Flowering response.*—Average of 4.8 open inflorescences 13 weeks after planting rooted cuttings.

*Lastingness of individual flowers on plant.*—8 to 9 days at 18° C.

*Fragrance.*—None.

*Peduncle.*—Color: RHS 143C (light-green). Length: 10.4 cm. Diameter: 0.3 cm. Texture: Appears glabrous.

*Pedicel.*—Color: RHS 143C (light-green), often one side RHS 184A (brown). Length: 2.1 cm. Diameter: 0.2 cm, with a spur near the flower base. Texture: Dense, very short pubescence.

Corolla:

*Shape of corolla.*—Nearly round outline, relatively large, occasionally with a gap between upper and lower petals, inner petals are more upright and somewhat irregularly directed.

*Form.*—Double.

*Diameter.*—5.4 cm.

*Number of petals.*—About 17 to 22.

*Petaloids.*—Shape: Variable, narrower and shorter than the petals, lower part is often threadlike or tube-shaped. Number: 2 to 3. Color: Variable from RHS 155A (white) at the base to RHS N74B (roughly the petal color) at the upper end.

Petals:

*Shape.*—Obovate.

*Apex.*—Rounded.

*Base.*—Attenuate or acute.

*Margin.*—Usually entire.

*Texture.*—Smooth.

*Upper petals.*—Length: 3.1 cm. Width: 2.8 cm. Color: Upper surface: RHS N74B (purple). Lower surface: RHS 72C. Markings: RHS 69D to RHS 155D (whitish) streak, framed by RHS 61A (red-purple) veins and a dot, in the middle of the petal, these markings are often covered by inner petals and not visible.

*Lower petals.*—Length: 2.9 cm to 3.1 cm. Width: 2.1 cm. Color: Upper surface: RHS 74A. Lower surface: Near RHS 71D. Markings: Absent.

Sepals:

*Number.*—5.

*Color.*—RHS 143C (light-green) for both surfaces, the largest sepal may be infused with RHS 174B (brownish).

*Length.*—1.3 cm.

*Width.*—Largest upper sepal: 0.5 cm. Other sepals: 0.3 cm.

*Shape.*—Ensiform.

*Apex.*—Acute.

*Base.*—Fused.

*Margin.*—Entire.

*Texture.*—Relatively long, fine hairs.

Reproductive organs:

*Androecium.*—Number of anthers: 5. Filament color: Mainly RHS 155D (white) to RHS 74D at upper surface. Filament length: Up to 0.9 cm. Filament diameter: 0.1 cm. Pollen color: RHS 16A (yellow-orange). Pollen amount: Moderate.

*Gynoecium.*—Pistil: Number: 1. Length: About 1 cm. Diameter: 0.1 cm. Stigma color: RHS 61A (dark-purple). Stigma shape: 5- to 6-lobed. Style color: RHS 69D to RHS 155D (whitish). Style length: 0.4 cm. Style shape: Filiform (filament-like) with the lobes of the stigma at right angles.

Fruit and seed set: No seed set observed.

Disease and insect resistance: No particular resistance or susceptibility has been observed.

COMPARISON WITH PARENTAL AND COMMERCIAL CULTIVARS

'Free Orch' differs from the female parent '8736-3' (unpatented) by having lavender-purple flowers, while '8736-3' has cherry-rose flowers. In addition, 'Free Orch' has more petals and an earlier flowering response in the Spring than '8736-3'.

'Free Orch' differs from the male parent '8732-5' (unpatented) by having deeper, lavender-purple flowers than '8732-5'. In addition, 'Free Orch' has a more compact plant habit and an earlier flowering response than '8732-5'.

'Free Orch' differs from the commercial variety 'Fiscomedy' (U.S. Plant Pat. No. 9,394) by having smaller, yet tighter and more evenly shaped inflorescences than 'Fiscomedy'. In addition, 'Free Orch' has smaller leaves and a more compact plant habit than 'Fiscomedy'.

'Free Orch' differs from the commercial variety 'Fisdel' (U.S. Plant Pat. No. 10,366) by having deeper, lavender-purple flowers and lighter-green foliage than 'Fisdel'. In addition, 'Free Orch' has smaller and tighter umbels than 'Fisdel'.

I claim:

1. A new and distinct cultivar of *pelargonium* plant as shown and described herein.

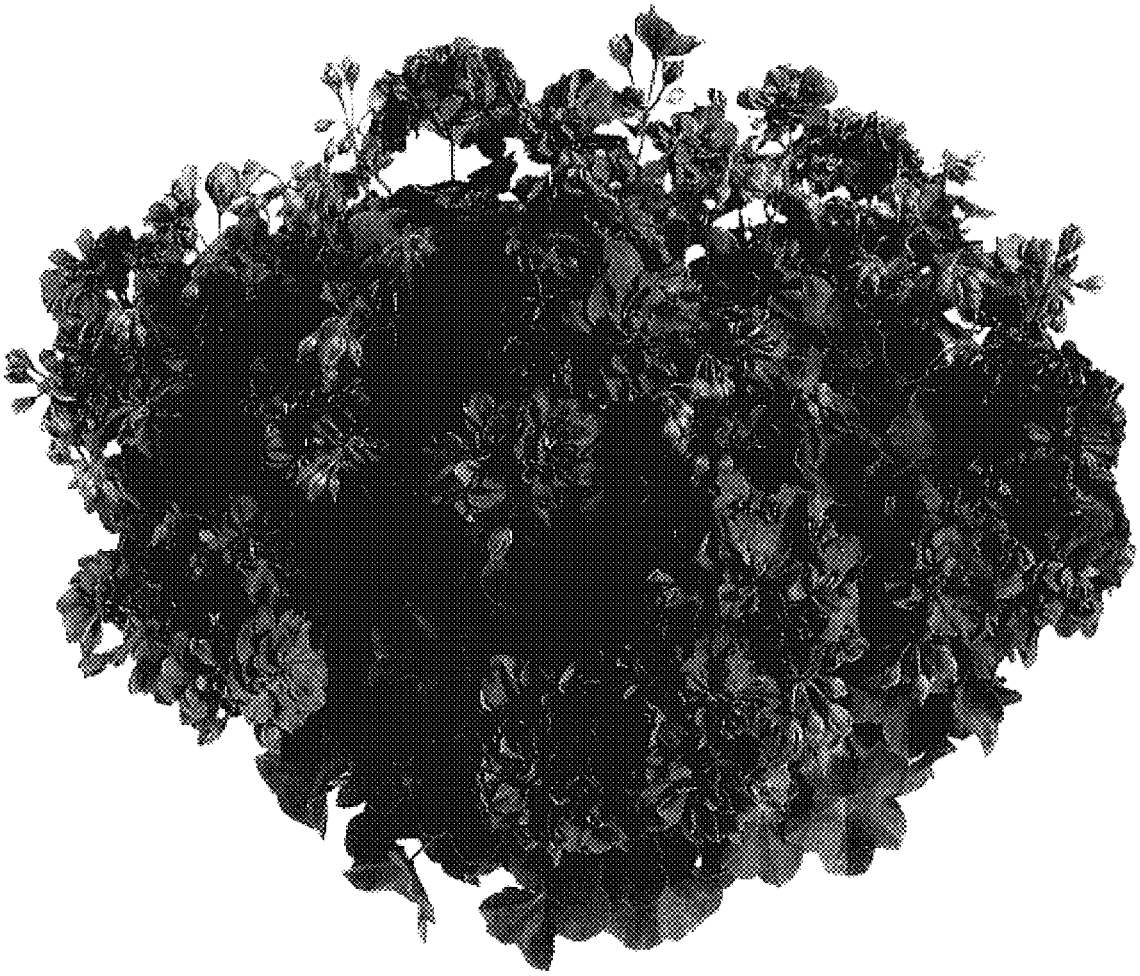

* * * * *